United States Patent [19]

Hummel

[11] Patent Number: 5,279,945
[45] Date of Patent: Jan. 18, 1994

[54] METHOD FOR THE ENZYMATIC DETERMINATION OF ASPARTAME

[75] Inventor: Werner Hummel, Titz, Fed. Rep. of Germany

[73] Assignee: Forschungszentrum Juelich GmbH, Juelich, Fed. Rep. of Germany

[21] Appl. No.: 760,681

[22] Filed: Sep. 16, 1991

[30] Foreign Application Priority Data

Sep. 17, 1990 [DE] Fed. Rep. of Germany ....... 4029296

[51] Int. Cl.$^5$ .............................. C12Q 1/37
[52] U.S. Cl. ........................ 435/24; 435/23; 435/25; 435/26; 435/288; 435/808; 435/810
[58] Field of Search ...................... 435/24, 23, 25, 26, 435/288, 808, 810

[56] References Cited

FOREIGN PATENT DOCUMENTS

0188712B1  7/1986  European Pat. Off. .
63-129996  6/1988  Japan .
63-219399  9/1988  Japan .

OTHER PUBLICATIONS

A. Mulchandani et al; Analytica Chimica Acta, 234, (1990) pp. 465–469.
G. G. Guilbault et al; Analytica Chimica Acta, 206, (1988), pp. 369–374.
O. Fatibello-Filho et al; Anal. Chem. 60, (1988), pp. 2397–2399.
P. Schadewaldt et al; Clinica Chimica Acta, 183, (1989) pp. 171–182.
W. Hummel et al; Appl Microbiol Biotechnol, 21 (1985) pp. 7–15.

*Primary Examiner*—Ronald W. Griffin
*Assistant Examiner*—Pamela S. Webber
*Attorney, Agent, or Firm*—Foley & Lardner

[57] ABSTRACT

The aspartame content in aqueous solutions is determined by enzymatic cleavage of aspartame to aspartic acid and phenylalanine methyl ester by means of a peptidase, followed by a detection reaction cocatalyzed by adenine dinucleotide. The phenylalanine is, after elimination of the ester group by means of chymotrypsin, converted by phenylalanine dehydrogenase in the presence of NAD$^+$ into phenylpyruvate, and the aspartame concentration is measured via the NADH or NH$_3$ formation which occurs as a consequence. Alternatively, the aspartic acid is converted by a cell extract which acts on aspartic acid in the presence of NADP$^+$, and the resultant NADPH or NH$_3$ is used to determine aspartame concentration. These enzymatic reactions preferably are carried out in consecutive enzyme columns with carrier-immobilized enzymes by the FIA technique. The proportion of hydrolysis products can be measured by analyzing another sample omitting the peptidase reaction. The enzymatic cell extract used for the aspartic acid determination is obtained from microorganisms which are isolated from decomposing organic matter. Preferably used for this purpose is the strain DSM 6705. The cell extract can be used as crude extract, without special purification for the analysis, and is generally suitable for detecting aspartic acid.

12 Claims, 4 Drawing Sheets

METHOD FOR THE ENZYMATIC DETERMINATION OF ASPARTAME

BACKGROUND OF THE INVENTION

The present invention relates to a method and to a device for determining the content of L-α-aspartyl-L-phenylalanine methyl ester (Asp-PheOMe or "aspartame") in aqueous solution via enzymatically cleaving aspartame to aspartic acid and phenylalanine methyl ester, by means of a peptidase and subsequent enzymatic detection reaction. The invention further relates to an enzymatically active cell extract suitable for this purpose.

The sweetener aspartame is a dipeptide ester composed of the two L-amino acids aspartic acid and phenylalanine, which has, because of its high sweetening power and physiological acceptability, been approved in many countries within a short time and whose production is now of the order of several 1000 tons annually.

Examples of important uses for this sweetener are refreshing beverages, sweetener tablets and sweetener powders, desserts, fruit yoghurt and chewing gum.

Aspartame is completely stable only in solid form at room temperature and, in aqueous solutions, its stability depends on the time, the temperature and the pH. Possible products of hydrolytic degradation are aspartylphenylalanine, phenylalanine methyl ester, aspartic acid and phenylalanine. Hence, there is considerable interest in an analytical method for aspartame which displays maximum selectivity and is easy to implement.

Principal areas of use for such a method include process control in the production of the dipeptide and quality control for final products (foodstuffs), especially given the limited storage stability of aspartame. For example, the taste of refreshing beverages is retained only when a storage temperature of 20°-25° C. is maintained and the beverage is consumed within about 5 weeks. Another area of use for an analytical method for aspartame is in medicine where degradation and excretion rates have to be determined in biological samples, such as serum and urine.

It is common knowledge that aspartame analysis is usually carried out by HPLC. See, for example, J. A. Stamp & T. P. Labuza, J. Food Science 54: 1043–46 (1989). In addition, determination methods have been described which used thin-layer chromatography, capillary isotachophoresis, gas chromatography and ion-exchange chromatography, as well as amino-acid analysis. These methods demand considerable effort and are generally less suitable for high sample frequencies.

There are also already analytical methods for determining aspartame concentrations which are based on an enzymatic reaction.

In Anal. Chem. 60: 2397-99 (1988), O. Fatibello-Filho et al. describe an analytical method for determining aspartame concentration which is based on an enzymatic reaction thereof, initially with carboxypeptidase A to eliminate L-aspartic acid, and subsequent conversion with L-aspartase into fumarate and ammonia. In this case the enzymes are co-immobilized on the gas membrane of an electrode which reacts with the ammonium ions formed.

A similar method from the same research group is described by G. G. Guilbault et al., Anal. Chim. Acta 206: 369-74 (1988). This method also uses an ammonium-selective electrode on which L-aspartase is immobilized and is used to bring about direct conversion of aspartame with elimination of ammonia. In addition, the authors outline various enzymatic degradation routes, some of which take place over several stages and are said in general to take place with the evolution of ammonia. However, these methods have not been investigated in detail.

Finally, in Anal. Chim. Acta. 234: 465-69 (1990), an analytical method for aspartame is taught whereby peptidase is used to eliminate aspartic acid, which is converted in the presence of α-ketoglutarate by means of aspartate aminotransferase to L-glutamate. The assay is based on the enzymatic oxidation of the L-glutamate by glutamate oxidase and a determination of the resultant oxygen consumption.

A problem plaguing these enzymatic analytical techniques is the relatively low stability of L-aspartase. As a consequence, the information provided by a given assay is not necessarily unambiguous.

SUMMARY OF THE INVENTION

It is therefore an object of the present invention to provide an analytical method for determining aspartame concentration which can be carried out with relatively stable and readily available enzyme products, which takes place smoothly, and which provides reliable information.

The method according to the present invention has been developed for this purpose and comprises bringing about an enzymatic reaction for detecting the products thereof which is cocatalyzed by adenine dinucleotide, by either (a) reacting the resulting aspartate acid by means of an enzyme-containing cell extract which converts aspartic acid in the presence of $NADP^+$, with the addition of $NADP^+$, and measuring the concentration of the aspartame via the formation of NADPH or $NH_3$ or (b) detaching the ester group from the phenylalanine methyl ester enzymatically by means of chymotrypsin and converting the resulting L-phenylalanine enzymatically by means of phenylalanine dehydrogenase in the presence of $NAD^+$ into phenylpyruvate, and measuring the aspartame concentration via the formation of NADH or $NH_3$.

It is also an object of the invention to provide a device for easily and quickly carrying out the method of the invention.

It is a further object of the invention to provide a cell extract which can be used to carry out the invention.

In accordance with this and other objects of the invention, a method for the quantitative determination of L-α-aspartyl-L-phenylalanine methyl ester in aqueous solution is provided.

The method provides for an enzymatical oxidation of one of the amino acids contained in said dipeptide ester by a cocatalyzed enzymatic reaction forming $NH_4^+$ and hydrogenated cocatalyst and detecting one of said formed $NH_4^+$ and hydrogenated cocatalyst physically after an enzymatic cleavage of said peptide ester.

Thus the L-α-aspartyl-L-phenylalanine methyl ester is at first enzymatically converted by a peptidase into aspartic acid and phenylalanine methyl ester, and then providing reaction products selected from alternative groups of reactions.

In a first embodiment of the invention, one group of reactions provides for enzymatically cleaving the phenylalanine methyl ester into phenylalanine and methanol; and then reacting the phenylalanine with nicotinamide adenine dinucleotide (NAD+) in the presence of a phenylalanine dehydrogenase to produce phenylpyruvate, $NH_4+$, and NADH.

A second embodiment provides for reacting the aspartic acid with nicotinamide adenine dinucleotide phosphate (NADP) in the presence of a cell extract which catalyzes the NADP+-dependent conversion of aspartic acid in the presence of NADP+ to produce an aspartic reaction product, $NH_4+$, and NADPH.

The reaction products of either of the embodiments are then measured by conventional means. The measuring of the concentration is performed on one of the reaction products from the group consisting of NADH, $NH_4+$ and NADPH. The cleaving of the L-­-aspartyl-L-phenylalanine methyl ester is in the presence of a peptidase and the cleaving of the phenylalanine methyl ester is performed in the presence of chymotrypsin.

Preferably, the enzymes are immobilized on a carrier of finely divided microporous inert material by chemical groups capable of attachment to the inert material. A specifically preferred material is an activated $SiO_2$ having especially, pores of the order of 500 Å. Preferably, the enzymes are provided in consecutively connected vessels of a device through which buffer solution continuously flows from an injection port end through the vessels into a reaction product end, the reaction product end having means for detecting and measuring the reaction products.

The method is preferably practiced by injecting a solution to be analyzed into the injection end for consecutive flow through the enzyme vessels and the detector and injecting a solution of one of NADP+ or NAD+ concomitant to the sample latest before the entrance of the (in flow direction) last enzyme vessel. Preferably, the solutions are simultaneously injected into the injection end and thoroughly mixed before entering the vessels containing the enzymes. The concentration of one or more of the $N_4+$, NADH and NADPH is determined physically, for instance, by fluorimetry. However, any other means of detection known in the art can be used.

In accordance with additional objects of the invention, the method provides for the determination of a background value of possible interfering reactants in a sample. The measured values of identical samples analyzed after one has been exposed to peptidase, chymotrypsin and phenylalanine dehydrogenase and the other has been exposed only to chymotrypsin and phenylalanine dehydrogenase are compared to determine this background value. The background value obtained thereby is then subtracted from the measured value of the identical sample to obtain the corrected value of the aspartame concentration.

Also provided is an enzymatic cell extract capable of catalyzing the reaction of aspartic acid with NADP+ to form NADPH and $NH_3$, the extract being obtained from cell isolates from decomposing organic matter. The enzymatic cell extract of claim 13, obtained from the strain Asp-1 of Deposit No. DSM 6705 and mutants thereof. A background value could be detected in this case analogously to the above indicated manner.

In accordance with still other objects of the invention, a device for the quantitative determination of aspartame in aqueous solution is provided. The device provides a first vessel containing an inert carrier and, immobilized on the carrier, peptidase for enzymatically cleaving L-α-aspartyl-L-phenylalanine methyl ester into aspartic acid and phenylalanine methyl ester, and either, a second vessel containing an inert carrier and, immobilized on the carrier, chymotrypsin for enzymatically cleaving the phenylalanine methyl ester into phenylalanine and methanol, and a third vessel containing an inert carrier and, immobilized on the carrier, phenylalanine dehydrogenase for catalyzing the reaction of the phenylalanine with NAD+ to produce, phenylpyruvate, $NH_4+$ and NADH; or a fourth vessel (instead of said second and third vessels) containing an inert carrier and, immobilized on the carrier, a cell extract for catalyzing the reaction of the aspartic acid with NADP+ to produce an aspartic reaction product, $NH_4+$ and NADPH. Also provided in the device are means for conveying a sample and coenzymes (cocatalysts) sequentially either, through the first vessel and then the second vessel and then the third vessel, or through the first vessel and then the fourth vessel, means for introducing the sample and the reactants into the device, and means for determining the concentration of resultant products.

Preferably, the device further provides means for mixing the sample and the reactants after the introducing and before the sample and the reactants enter the vessels. Preferably, a fluorimeter is provided for the detection of NADH or NADPH. In addition, the device has conduits for conveying a continuously flowing liquid stream and valves for directing the stream through the reactant vessels.

Yet further in accordance with other objects in the invention, the device is provided with a cell extract obtained from the strain Asp-1 of Deposit No. DSM 6705 and mutants thereof, immobilized on a carrier and contained in a fourth vessel.

It should be understood that although the method and device described herein can be practiced within the parameters as described, that other methods and devices are obvious from the disclosure given herein, and that the device and method of the present invention are not limited to the preferred embodiments.

DETAILED DESCRIPTION OF PREFERRED EMBODIMENTS

In accordance with the present invention, the enzymatic conversions employed in each case for the determination take place with the addition of nicotinamide dinucleotide coenzyme and produce coenzyme hydrogenation products which can be readily detected by known physical means.

In accordance with one embodiment of the present invention, aspartame, in the presence of a peptidase, is cleaved to aspartate and phenylalanine methyl ester. The phenylalanine methyl ester, in the presence of chymotrypsin, is then cleaved to phenylalanine and methanol. The resultant phenylalanine, in the presence of phenylalanine-DH, is reacted with NAD+ to produce phenylpyruvate, $NH_4^+$ and NADH. Either of the coenzyme products $NH_4^+$ or NADH can then be quantitatively determined by known physical means, NADH, e.g., by fluorimetry. This embodiment is illustrated by the following equations:

A phenylalanine DH which can be used is described in EP-C 188 712.

Figure 1:
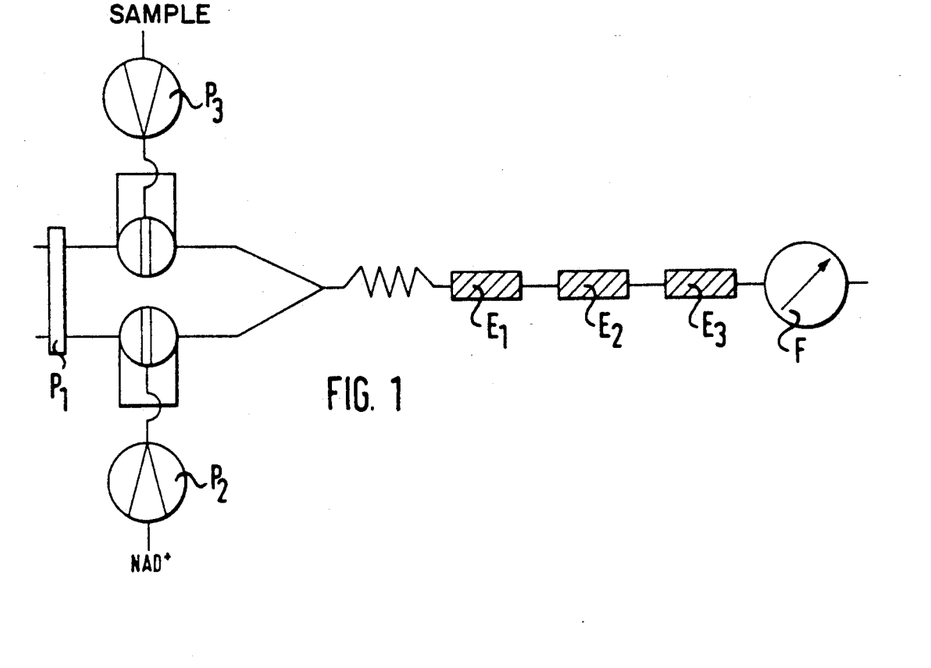
FIG. 1 is a line drawing which schematically shows a device for flow injection analysis of aspartame in accordance with a first embodiment of the present invention.
Figure 2:
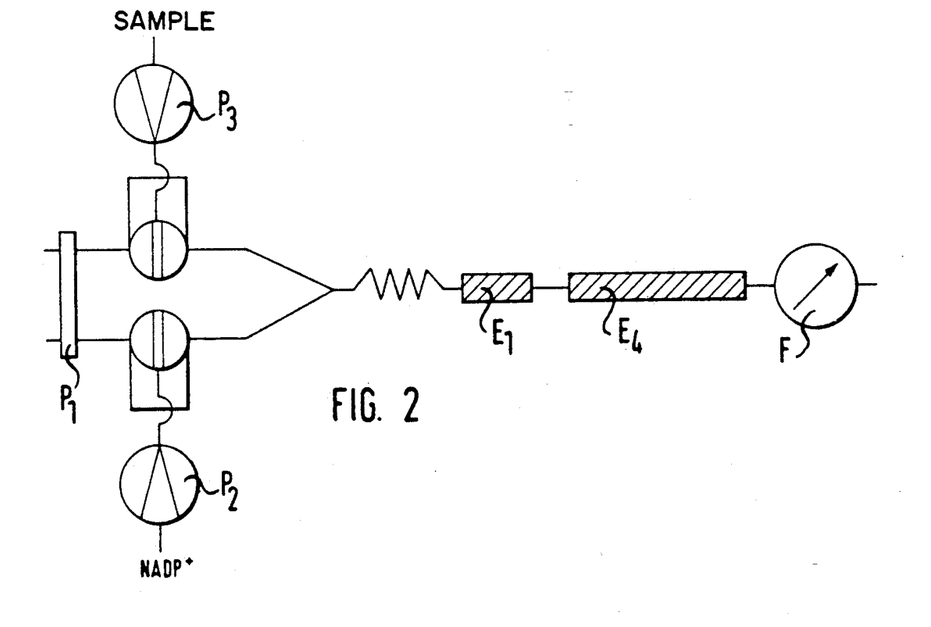
FIG. 2 is a line drawing which schematically depicts a device for flow injection analysis of aspartame in accordance with a second embodiment of the invention.

In a second embodiment of the present invention, a quantitative determination of aspartame can be carried out using a novel cell extract which has enzymatic activity. As in the first embodiment, aspartame, in the presence of a peptidase, is cleaved to aspartate and phenylalanine methyl ester. The resultant aspartate is then reacted with NADP+ in the presence of the cell extract to form NADPH and $NH_4^+$. The chemical nature of the "aspartate reaction product" has not been identified as out of interest. Probably it may be oxalacetate. The NADPH and $NH_4^+$ are reaction products which can be quantitatively determined by known physical means such as those applicable to the first embodiment. This second embodiment is illustrated by the following equations:

Both methodological variants can be carried out to particular advantage in the context of a flow injection analysis (FIA), for which flow diagrams are indicated in FIGS. 1 and 2 attached. This entails the enzymes being employed in immobilized form in consecutive columns through which is passed a carrier stream which is formed by buffer solution and into which both the sample and a defined concentration of the particular coenzyme are injected. The NADPH or NADH produced, respectively, in enzymatic reaction 5 or 3 is determined, in particular by fluorimetry, and is used as a measure of the aspartame concentration in the sample.

Various peptidases are available to the person skilled in the art for the peptide cleavage. Pronase ® primarily was used in the examples detailed herein.

The aspartame determination by means of phenylalanine-DH is thus carried out as follows:

(1) The aspartame-containing sample passes through the Pronase ®-containing enzyme column, where aspartame is cleaved to aspartic acid and phenylalanine methyl ester.

(2) The sample then passes through the chymotrypsin-containing second column, where the resulting phenylalanine methyl ester is cleaved to phenylalanine and methanol.

(3) The sample then passes through the third column which contains the enzyme phenylalanine dehydrogenase. Phenylalanine here undergoes oxidative deamination with reduction of the coenzyme. The resulting reduced coenzyme NADH can be quantified as a measure of the aspartame concentration (e.g., by measuring the fluorescence) although it is also possible, of course, to quantify the produced ammonium ion.

In place of NADH determination by fluorimetry, it is possible to provide any other physical detection method, such as, for example, determination by photometry or amperometry.

With this design, background reactions not based on aspartame can be easily determined by injecting another aliquot of the sample in such a way that the sample passes through only the chymotrypsin and phenylalanine dehydrogenase columns. This provides a quantitative measure of the phenylalanine and its ester which are already present without cleavage and can be used for correction of the assay results.

The analytical method is possible only because of the spatial separation of the three enzymes because two of the enzymes employed (Pronase ® or peptidase and chymotrypsin) are proteases which would inactivate both the phenylalanine dehydrogenase and each other. Photometric cuvette assays based on these enzymes, for example, are impossible. Thus FIA-techniques are preferred, though other methods of spatial separation e.g. immobilisation on separate positions of a membrane are useful.

An enzymatically active cell extract has been found for determining the aspartame content by means of a co-catalyzed aspartic acid conversion. It can be used as crude extract and carries out NADP-dependent conversion of aspartic acid with the formation of $NH_3$ and NADPH.

Thus, in this variant of the analysis, in place of the above-mentioned steps 2 and 3, the sample coming from the Pronase ® (peptidase) column 1 passes through another column containing carrier-immobilized enzymatic reactive cell extract.

The crude extract is obtained from microorganisms which have been obtained by means of a screening process from soil samples, especially from composting samples.

It has been possible to isolate suitable strains from various soil samples by the method described hereinafter in Example 5, such as, for example, from samples of surface soil in deciduous woods, domestic (mixed) compost and municipal composting plants.

Detailed investigation was carried out in this connection on an organism which was called Asp-1 and has been deposited under No. DSM 6705 at the Deutsche Sammlung von Mikroorganismen in Braunschweig.

The crude extract obtained from these organisms is, of course, not only suitable for aspartame determination but can also be used in general as catalyst for enzymatic determination of aspartic acid.

The present invention is described further below by reference to the following, illustrative examples.

EXAMPLE 1. Peptidase cleavage of aspartame

To investigate the peptide cleavage, 10 mM aspartame dissolved in 100 mM tris-HCl buffer, pH 7.5 (with 10 mM $CaCl_2$), was mixed with 2 units of a peptidase and incubated at 30° C. Samples (50 µl each) were taken after 10 to 20 min, and the enzymatic cleavage reaction was stopped by adding 200 µl of acetic acid (pH 2.2). The aspartate liberated from aspartame by proteolytic action was quantitatively determined with the aid of an amino-acid analyzer and was used as a measure of the cleavage activity.

Of the peptidases investigated, the Pronase® supplied by Boehringer Mannheim showed particularly high activity (214 nMol of aspartate being liberated per min/ml with Pronase®). The enzyme known as Pronase® is a mixture of peptidases, esterases and proteases which contains the aspartame-specific peptidase enzyme which is active in the mixture.

EXAMPLE 2. Immobilization of Pronase®, chymotrypsin and phenylalanine dehydrogenase It is possible to use for the immobilization, for example, commercially available porous solids which have already been treated in a suitable manner for the coupling of enzymes (activated). The following were specifically employed:

A. Immobilization of Pronase®

53 mg of $SiO_2$ carrier[1] (pore size 540 Å; supplied by Mobitec, Göttingen, FRG) were suspended in 400 µl of potassium phosphate buffer (ph 7.0), and to this were added 100 µl of Pronase®-solution (17.5 mg/350 µl $H_2O$ = 122.5 U/350 µl $H_2O$). This suspension was gently shaken at 4° C. for 30 min and then left to stand at 4° C. for 20 h. It was then washed on a frit with 500 ml of tris-HCl buffer (0.1M; pH 7.0), and this buffer was used for storage of the immobilisate. The enzymatic activity of this immobilisate was determined by the following assay:
[1] Mobitec carrier activated by isocyanate groups 500 µl of a 10 mM aspartame solution (dissolved in 100 mM tris-HCl buffer, pH 7.5 (with 10 mM $CaCl_2$)) were mixed with 33 mg of Pronase®-containing immobilisate and incubated at 30° C. Samples (50 µl each) were taken after 10–20 min, and the enzymatic cleavage reaction is stopped by addition of 200 µl of acetic acid (pH 2.2). The aspartate liberated from aspartame by proteolytic action was determined quantitatively with the aid of an amino-acid analyzer and was used as a measure of the cleavage activity (1 enzyme unit (1 U) is the amount of enzyme which forms 1 µmol of aspartate/min).

The immobilization under these conditions provided a carrier with 7.7 U of Pronase® per 1 g of carrier.

B. Immobilization of chymotrypsin 51 mg of $SiO_2$ carrier (pore size 540 Å; supplied by Mobitec, Göttingen, FRG) was suspended in 400 µl of potassium phosphate buffer (pH 7.0), and to this was added 50 µl of chymotrypsin solution (4 mg (360 U)/ml $H_2O$). This suspension was gently shaken at 4° C. for 30 min and then left to stand at 4° C. for 20 h. It was then washed on a frit with 500 ml of tris-HCl buffer (0.1M; pH 7.0), and this buffer was used to store the immobilisate. The enzymatic activity of this immobilisate was determined by the following assay:

500 µl of a 10 mM solution of L-phenylalanine methyl ester (dissolved in 100 mM tris-HCl buffer, pH 7.5 (with 10 mM $CaCl_2$)) was mixed with 34 mg of Pronase®-containing immobilisate and incubated at 30° C. Samples (50 µl each) were taken after 10–20 min, and the enzymatic cleavage reaction was stopped by addition of 200 µl of acetic acid (pH 2.2). The L-phenylalanine liberated from the methyl ester by the enzymatic action was quantitatively determined with the aid of an amino-acid analyzer and was used as a measure of the cleavage activity (1 enzyme unit (1 U) is the amount of enzyme which forms 1 µmol of phenylalanine/min).

The immobilization under these conditions provided a carrier with 4.88 U of chymotrypsin per 1 g of carrier.

C. Immobilization of phenylalanine dehydrogenase 55 mg of $SiO_2$ carrier (pore size 540 Å; supplied by Mobitec, Göttingen, FRG) was suspended in 400 µl of potassium phosphate buffer (pH 7.0), and to this was added 100 µl of phenylalanine dehydrogenase solution (170 U/ml). This suspension was gently shaken at 4° C. for 30 min and then left to stand at 4° C. for 20 h. It was then washed on a frit with 500 ml of tris-HCl buffer (0.1M; pH 7.0). The bound activity was measured by the following assay: 20 mg of immobilized enzyme, 400 µl of ammonium formate buffer (0.1M; pH 8.3), 10 µl of formate dehydrogenase (50 U/ml), 50 µl of phenylpyruvate (50 mM) and 25 µl of NADH (10 mM) were mixed. Samples were taken after 10–20 min, stopped by addition of acetic acid, and the phenylalanine produced in each case by enzymatic reaction was measured with the aid of an amino-acid analyzer (Biotronik 6001, Munich, FRG; separating program for protein hydrolysates). 1 Enzyme unit (1 U) is the amount of enzyme which forms 1 µmol of phenylalanine/min. This resulted in carriers with an enzyme content of 6–8 U/g of carrier.

EXAMPLE 3. Design of an analytical system for aspartame determination and calibration FIG. 1 shows the diagrammatic design of the analytical system (flow injection analysis principle). $P_1$, $P_2$ and $P_3$ are peristaltic pumps; a dual injection valve supplied by Tecator (40 µl) was employed for simultaneous injection of sample and coenzyme into the buffer stream. The contents of the enzyme-containing columns E were: $E_1$, Pronase; $E_2$, chymotrypsin; and $E_3$, phenylalanine dehydrogenase. F is a fluorescence photometer.

It is, of course, also possible to add the $NAD^+$ elsewhere as long as it is available for the dehydrogenase reaction.

The NADH concentration was measured with the aid of a fluorescence detector (Merck F-1050; Merck, Darmstadt, FRG) with the excitation wavelength 340 nm and the absorption wavelength 460 nm. The immobilized enzymes were packed into Plexiglass columns (length 15 mm, internal diameter 3 mm), escape of the immobilisate being prevented by fine-mesh plastic networks.

A buffer stream (0.05M tris-HCl, pH 8.5 with 10 mM $CaCl_2$) flowed continuously at a flow rate of 1.1 ml/min through the columns and the detector. The sample was injected instantaneously with the aid of the injection valve into the buffer stream and, because of the constant flow rate, passed through the three enzyme columns with a reproducible residence time.

Figure 3:
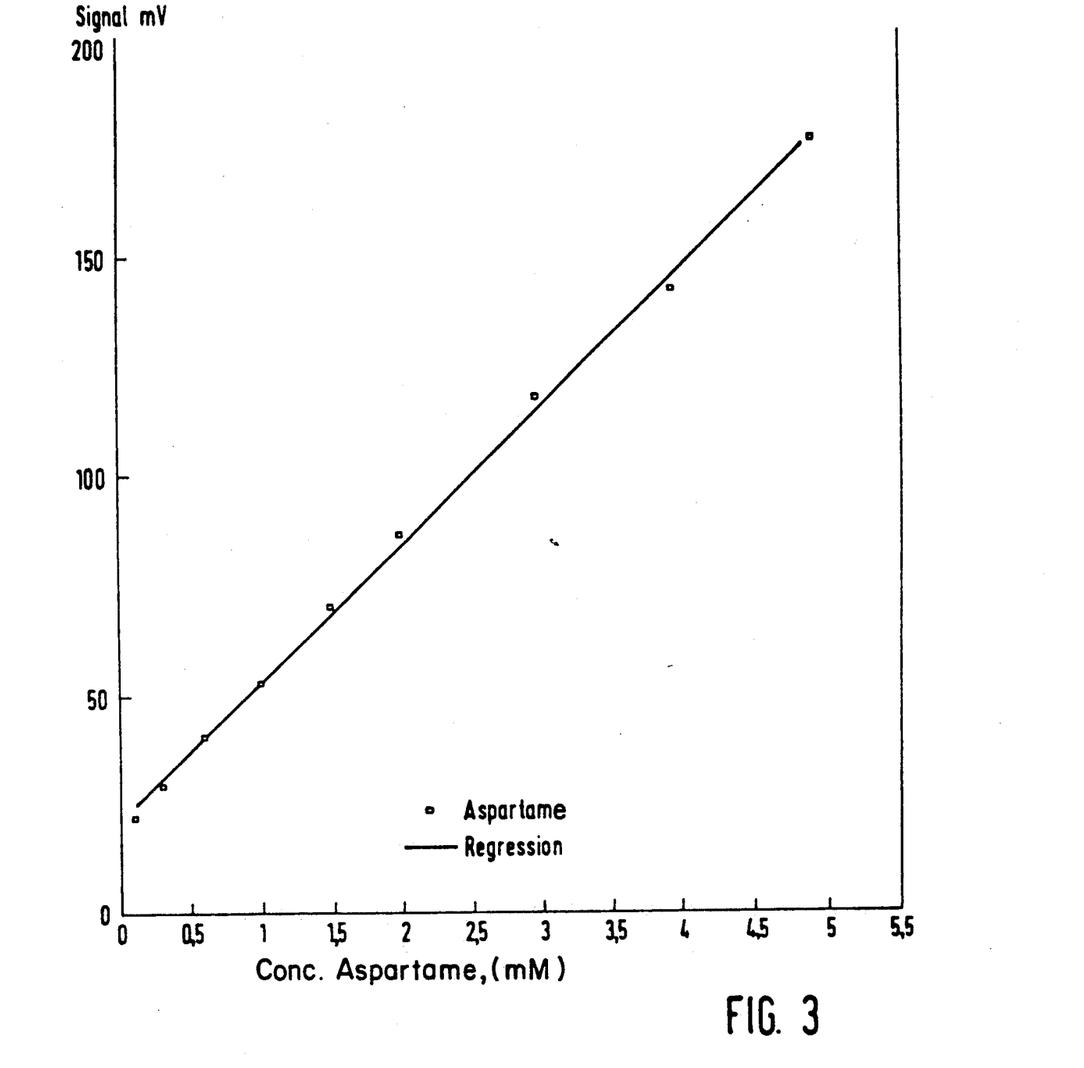
FIG. 3 is a graph which shows the relationship between detector signals and aspartame concentration on analysis of aspartame by the FIA technique employing phenylalanine-DH.

Aspartame concentrations in the range 0.1–5 mM, dissolved in sodium acetate/acetic acid buffer (0.2M, pH 4.3) yielded a linear relation between the aspartame concentration and the fluorescence signal (FIG. 3).

The total measurement time with this design was 95 seconds, and the sample rate is at least 30 samples/hour.

EXAMPLE 4. Application of the analytical method to foodstuff samples

As an example of the applicability of the enzymatic determination method, the aspartame content in a sweetener tablet and in two foodstuffs sweetened with aspartame (strawberry yoghurt and peach quark, (a peach/cottage cheese mixture) supplied by Onken) was determined. As a check, the aspartame concentration was measured by means of an amino-acid analyzer. The samples were prepared as described below way for the enzymatic aspartame determination.

A sweetener tablet was dissolved in 20 ml of sodium acetate/acetic acid buffer (0.2M; pH 3.5), and 2 ml of this solution were then used for further sample preparation. 1.5 g of each of the two foodstuff samples were stirred with 0.5 ml of this acetate buffer. These three samples were mixed with 10 ml of propylene carbonate, treated in an ultrasonic bath for 5 min and then centrifuged at 5000 rpm for 3 min. The phase containing propylene carbonate was removed and dried by adding 2 g of $Na_2SO_4$ (anhydrous). After 2 hours, the solid was removed by filtration through a paper filter, diluted 1:10 with sodium acetate/acetic acid buffer (0.2M; pH 4.3), and the aspartame content was measured by means of the flow injection analysis described in Example 3. These results are compiled in Table 1. For the measurement with the amino-acid analyzer, the samples were taken up in sodium acetate/acetic acid buffer (0.2M; pH 2.2), centrifuged and filtered (0.45 μm filter) to remove solids and suspended matter and fractionated in an amino-acid analyzer (Biotronik 6001, Munich, FRG) with the separation program for protein hydrolysates. The elution time for aspartame under these conditions was 49.3 minutes, and this separation method can be calibrated using weighed aspartame standards.

The results are compared with those from the FIA in Table 1. The comparison shows that the enzymatic aspartame determination can be applied to foodstuff samples. More specifically, Table 1 shows the aspartame contents in foodstuff samples. Each sample was measured enzymatically and with the aid of an amino-acid analyzer.

TABLE 1

| Sample | Aspartame content (g/l) | |
|---|---|---|
| | Enzymatic (FIA) | Chromatography (amino-acid analyzer) |
| Sweetener tablet | 2.1 | 2.3 |
| Yoghurt | 1.9 | 2.0 |
| Quark | 2.0 | 2.1 |

The following comparative experiments were carried out for the carrier immobilization:

A. PRONASE ®

A.1. Immobilization on aminopropyl-CPG (CPG=Controlled Pore Glass), pore size 1400 Å (Fluka, Neu-Ulm, FRG):

Immobilization by the procedure of Stolzenbach, F. E. and Kaplan, N. O. (1976), Methods in Enzymology (Colowick, S. P. and Kaplan, N. O., eds.), vol. 44, pp 929–936, Academic Press, New York.

Coupling by the procedure with glutaraldehyde. 100 μl of Pronas ® solution (122.5 U/350 μl $H_2O$) were employed.

A.2. As A.1. but coupling by means of CMC (=1-cyclohexyl-3-(2-morpholinoethyl)carbodiimide (5 mg/ml)) was employed.

A.3 As in A.1. but coupling by means of EDAC (=1-ethyl-3-(3-dimethylaminopropyl)carbodiimide) was employed.

A.4. As in A.1. but BIORAN (supplied by Schott) with a pore size of 550 Å was employed in place of aminopropyl-CPG.

A.5. As in A.4. but the glutaraldehyde solution additionally contained 50 mg/ml sodium borohydride.

B. CHYMOTRYPSIN

B.1. As in A.2. but with 50 μl of chymotrypsin solution (360 U/ml) employed in place of Pronase.

B.2. As in A.3. but with 50 μl of chymotrypsin solution (360 U/ml).

C. PHENYLALANINE WITH DEHYDROGENASE

C.1. As in A.1. but with 100 μl of phenylalanine dehydrogenase (170 U/ml) in place of Pronase.

C.2. As in A.2. but with 100 μl of phenylalanine dehydrogenase (170 U/ml).

C.3. As in A.3. but with 100 μl of phenylalanine dehydrogenase (170 U/ml).

Table 2: Compilation of the results on immobilization of Pronase, chymotrypsin and phenylalanine dehydrogenase.

TABLE 2

| Method | Bound enzyme (U/g of carrier) | | |
|---|---|---|---|
| | Pronase | Chymotrypsin | Phenylalanine DH |
| Example 2.A. | 7.7 | | |
| A.1. | 3.9 | | |
| A.2. | 2.2 | | |
| A.3. | 2.4 | | |
| A.4. | 4.5 | | |
| A.5. | 3.3 | | |
| Example 2.B. | | 4.88 | |
| B.1. | | 0.73 | |
| B.2. | | 0.38 | |
| Example 2.C. | | | 8 |
| C.1. | | | 2 |
| C.2. | | | 6.5 |
| C.3. | | | 4 |

As is evident, the $SiO_2$ carrier activated with reactive isocyanate groups and supplied by Mobitec was particularly suitable.

EXAMPLE 5. Isolation of microorganisms with enzyme acting on aspartic acid

A. Isolation from soil samples

Suitable microorganisms were isolated from soil samples by applying suspensions of soil samples to nutrient medium solidified by adding agar. The nutrient medium had the following composition:

| L-aspartic acid | 10 g/l |
| Yeast extract | 0.1 g/l |
| $KH_2PO_4$ | 2 g/l |
| Trace salt solution | 20 ml/l |
| Agar | 18 g/l |

The pH was adjusted to 5.5, and the solution was sterilized at 121° C. for 20 minutes and then introduced into sterile Petri dishes.

The source of the microorganisms was soil samples which were suspended in sterile sodium chloride solution (9 g/l). For this, about 1 g of soil sample was mixed with 20 ml of sodium chloride solution and kept at room temperature while stirring gently for about 20 minutes. Serial dilutions of this suspension were prepared and plated out on the solidified nutrient medium. The plates were incubated at 30° C. and then, after two days, individual colonies were removed and isolated out under sterile conditions. Colonies were regarded as pure when both diluting streaks on plates and the microscopic appearance were homogeneous.

Pure colonies were transferred into liquid medium (above medium without agar; 100 ml in each case) in shaker flasks (500 ml Erlenmeyer flasks) and incubated on an orbital shaker at 120 rpm and at a temperature of 30° C. for 2 days. The cells were harvested by centrifugation, washed with buffer (0.1M potassium phosphate; pH 7.5) and finally suspended in buffer (2 ml of buffer per 1 g wet weight of bacteria). The cells in this suspension were disrupted by milling with glass beads (0.3 mm diameter). A clear cell-free supernatant (crude extract) was obtained by centrifugation and was employed for the enzyme assay. The isolates were assayed to find whether they were able to carry out $NADP^+$-dependent conversion of aspartic acid.

The enzyme assay was performed on a mixture having the following constituents:

| | |
|---|---|
| L-aspartic acid | 10 mM |
| Potassium phosphate buffer | 100 mM (pH 8.5) |
| $NADP^+$ | 1 mM |
| $MgCl_2$ | 1 mM |
| Crude extract | 5-20 μl/ml (corresponds to about 100 μg of protein/ml of assay) |

The complete mixture without $NADP^+$ was briefly incubated at 30° C. and then the reaction was started by adding $NADP^+$. The formation of NADPH was followed in a photometer at 340 nm, the measurement temperature being 30° C. To determine the enzyme activity, the extinction coefficient for NADPH was used to determine the maximum rate of NADPH formation. Possible background activity was measured by determination in an assay sample without aspartic acid. An enzyme unit (1 unit) was defined as the amount of enzyme which converts 1 μmol of NADPH in 1 minutes.

More than 200 isolates were obtained from the total of about 40 soil samples employed, and it was possible to isolate microorganisms with the required activity from several samples from a composting plant. The macroscopic appearance revealed that the organism was the same in all the cases and, by way of example, the isolate "Asp-1" was identified microbiologically and employed for the subsequent applications.

B. Taxonomic identification of the isolate Asp-1

The microbiological characterization showed that the strain Asp-1 should be assigned to the genus pseudomonas. The following specific properties were found:

Gram-negative rod-shaped cells, motile, strict aerob, oxidase positive, catalase positive, acid from glucose, degradation of mannose, no hydrolysis of starch, non-fluorescent.

The strain was deposited on Sep. 10, 1991 at the Deutsche Sammlung von Mikroorganismen, Braunschweig, under the number DSM 6705.

EXAMPLE 6. Characterization of the enzyme complex

A. Detection of the enzyme-dependent NADPH formation

In order to show the coupling of aspartic acid degradation and coenzyme NADP reduction, the following reaction solution was placed in a cuvette (the final concentrations are stated):
Tris-HCl buffer (0.125M; pH 8.5;)
L-aspartic acid (1.86 mM)
$NADP^+$ (1 mM)
$MgCl_2$ (1 mM)
Crude extract of strain Asp-1 (50 μl/ml)
The reaction temperature was 30° C.

The formation of NADPH was followed by photometry at 340 nm, a sample being taken at 1 min intervals for determination of the instantaneous aspartic acid concentration. At the same time, the increase in the absorption at 340 nM corresponding to the NADPH formation was measured. The aspartic acid concentration was determined by column chromatography using an amino-acid analyzer (Biotronik LC 5001), and the NADPH concentration was determined by calculation using the absorption coefficient for NADPH. Table 3 shows that the formation of NADPH is coupled to the degradation of aspartic acid.

TABLE 3

| Enzyme-catalyzed formation of NADPH and degradation of aspartic acid: | |
|---|---|
| Degraded aspartic acid formed [μM] | NADPH [μM] |
| 0 | 0 |
| 29 | 28 |
| 57 | 58 |
| 145 | 148 |
| 181 | 177 |

B. Detection of enzyme-coupled $NH_3$ formation

Samples were taken at various times from a complete reaction mixture, and the concentration of the remaining aspartic acid and of the $NH_3$ formed was determined with the aid of an amino-acid analyzer. In order for the reaction to go as near as possible to completion, the reaction was coupled with an NADPH-consuming reaction. As Table 3 shows, there was stoichiometric liberation of $NH_3$ on degradation of aspartic acid. For detecting this, the enzyme-catalyzed reduction of acetophenone to phenylethanol was used. It is known that this reaction is strictly NADPH-dependent. This enzyme was obtained as described in the literature, see Hummel, W., *Appl. Microbiol. Biotechnol.* 34: 15-19 (1990), and a preparation with a specific activity of 30 U/mg was employed.

The complete reaction mixture (1 ml final volume) contained the following constituents:
Tris-HCl buffer (0.1M; pH 9.0)
L-aspartic acid (10 mM)
$NADP^+$ (1 mM)
Acetophenone (10 mM)
$MgCl_2$ (1 mM)
Phenylethanol dehydrogenase (5 U/ml) and,
Crude extract from the strain Asp-1 (100 μl/ml).

After a reaction time of 20 minutes there was a degradation of 3.4 μmol/ml aspartic acid and formation of 3.5 μmol/ml $NH_3$, and after 60 min there was a degradation of 6.6 μmol/ml aspartic acid and formation of 6.5 μmol/ml $NH_3$.

C. Substrate specificity of the enzymatic reaction

Glutamic acid was assayed as substrate and as compound of analogous structure in order to rule out the possibility that the described enzyme is a glutamate dehydrogenase. L-Aspartic acid was replaced by L-glutamic acid in an assay as described in Example 2.A, and the reaction was followed by photometry (340 nm). No formation of NADPH was measured within 5 min. This shows that the enzyme complex from the strain Asp-1 is specific for L-aspartic acid.

Figure 4:
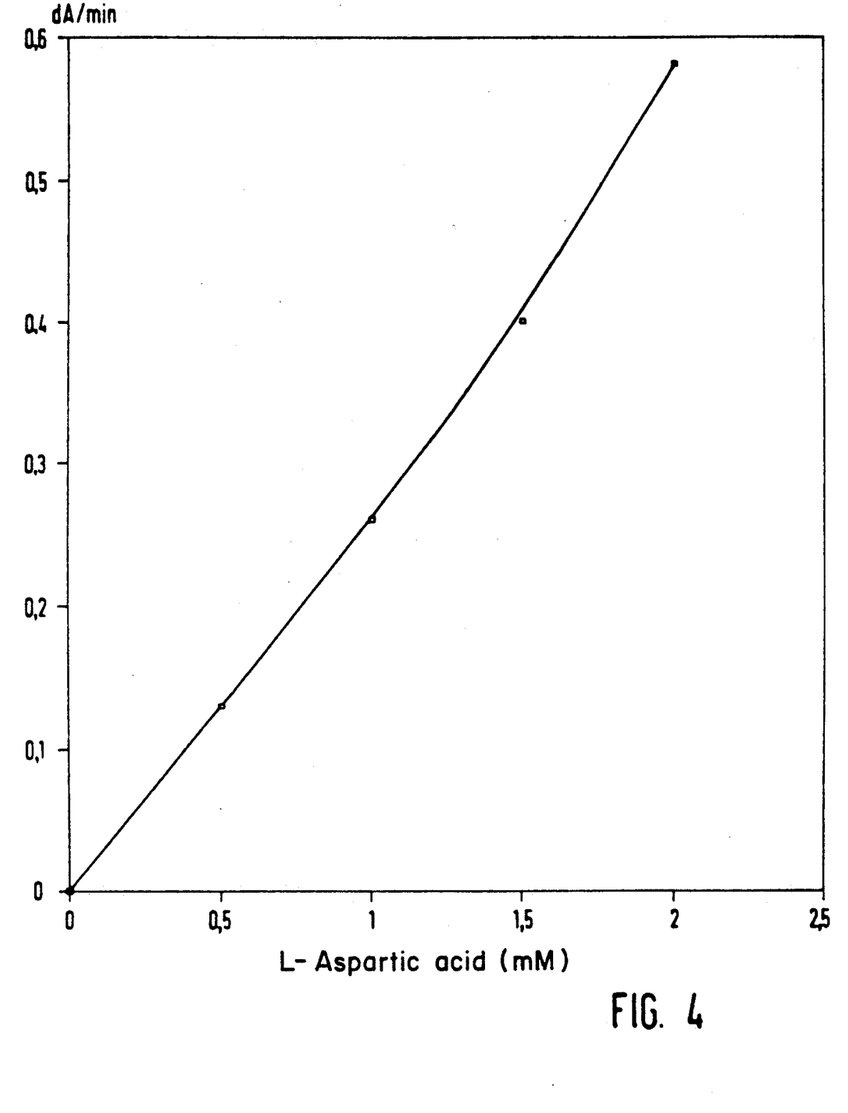
FIG. 4 is a graph illustrating the relationship between the rate of NADPH formation and L-aspartic acid concentration.

EXAMPLE 7. Use of the enzyme complex for the determination of the L-aspartic acid concentration The enzyme complex from the strain Asp-1 can be used to determine aspartic acid concentrations. As explained in Examples 2.A and 2.B, there is formation in the stoichiometric ratio of NADPH and of $NH_3$ from aspartic acid by the action of the enzyme. It is therefore possible to measure both the concentration of liberated $NH_3$ and that of NADPH by any analytical method for measuring aspartic acid. There are a number of analytical methods in existence for the measurement of $NH_3$. For example, an $NH_3$-sensitive electrode, gas analyzers or glutamate dehydrogenase can be used. We have measured the NADPH formation rate by photometry. For example, various aspartic acid concentrations were employed in the assay mixture described in Example 2.A, and the rate of NADPH formation (increase of NADPH/min) was determined as a function of the various aspartic acid concentrations. As FIG. 4 shows, there is a direct relation between the aspartic acid concentration employed in the range 0-2 mM and the measured NADPH formation rate.

EXAMPLE 8. Aspartame determination by means of enzymatic NADP-dependent aspartic acid determination Of the products formed by aspartame cleavage with Pronase, aspartic acid was chosen for determination of the content. The enzyme complex isolated from Asp-1 strain DSM 6705 was immobilized on a column E4 (FIG. 2), and the NADPH formed was measured by photometry with the aid of the detector.

Figure 5:
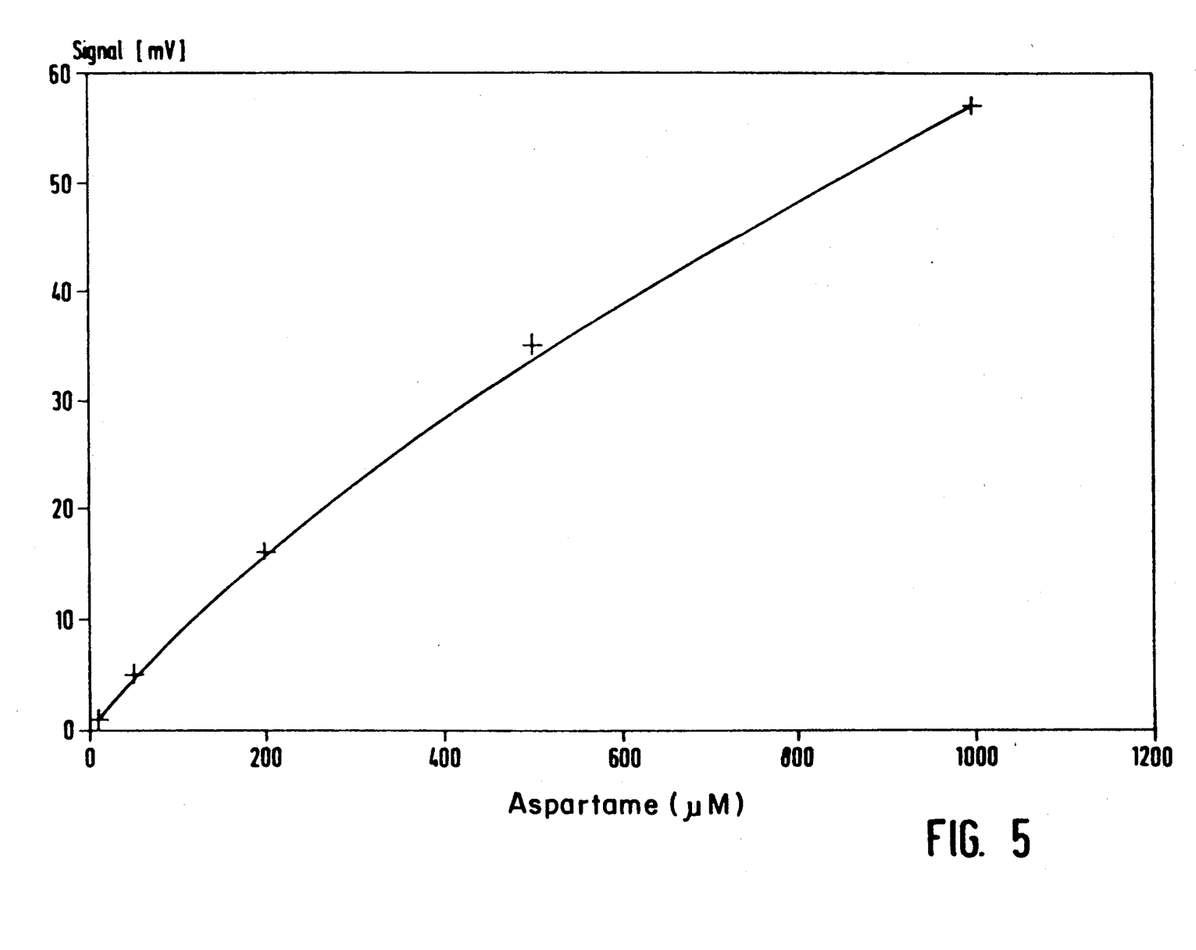
FIG. 5 is a graph which depicts the relationship between detector signals as a function of the aspartame concentration on analysis of aspartame by the FIA technique employing cell extract acting on aspartic acid. (If in the present specification the terms aspartate or asopartic acid are used, this means always that the aspartate ion will be present.)

For this assay, the enzyme complex was immobilized on a carrier in the manner described in Example 2. This immobilisate was then used, together with the immobilized Pronase, as described in Example 3, to determine by flow injection analysis the aspartame concentrations. In this case, the cell extract replaces the phenylalanine dehydrogenase, and the chymotrypsin column can be dispensed with. $NADP^+$ is employed in place of $NAD^+$ in this analytical method. FIG. 5 shows a calibration plot constructed with standard solutions of various aspartame concentrations and illustrates how the signal at the fluorescence photometer increases in proportion to the aspartame concentration.

What is claimed is:

1. A method for the quantitative determination of the dipeptide L-α-aspartyl-L-phenylalanine methyl ester in aqueous solution, comprising:
   (A) cleaving enzymatically said L-α-aspartyl-L-phenylalanine methyl ester, in aqueous solution, into aspartate and phenylalanine methyl ester by a peptidase suitable for such cleavage,
   (B) providing further reaction either by
     (ia) cleaving enzymatically said phenylalanine methyl ester into phenylalanine and methanol by chymotrypsin and
     (ib) reacting said phenylalanine with $NAD+$ in the presence of a phenylalanine dehydrogenase to produce phenylpyruvate, $NH_4^+$ and NADH or
     (ii) reacting said aspartic acid with $NADP^+$ in the presence of a cell extract which catalyzes the $NADP^+$-dependent conversion of aspartic acid in the presence of $NADP^+$ to produce an aspartic reaction product, $NH_4^+$ and NADPH; and
   (C) detecting physically at least one of said reaction products $NH_4^+$, NADH or NADPH to obtain a measured value corresponding to the amount of the dipeptide ester analyzed.

2. The method of claim 1, wherein, in step (C) NADH or NADPH are determined fluorimetrically.

3. The method of claim 1, wherein enzymes employed in said method are immobilized on an inert carrier.

4. The method of claim 3, wherein said enzymes are immobilized on granular microporous inert material by chemical groups capable of attachment to said inert material.

5. The method of claim 4, wherein said inert material is an activated $SiO_2$ having pores larger than about 500 Å.

6. The method of claim 3, wherein said enzymes are provided in a device having
   an injection port end,
   consecutively connected enzyme containers,
   a reaction product end, said reaction product end having means therein for detecting and measuring said reaction products, and
   buffer solution continuously flowing from said injection port end through said containers to said reaction product end.

7. The method of claim 6, further comprising the step of injecting a solution to be analyzed into said injection end for consecutive flow through said enzyme containers and said detector and an synchronized injection of a solution of one of $NAD+$ or $NADP+$ into said continuous flow latest in front of the entrance of the in flow direction last of said enzyme containers.

8. The method of claim 7, wherein said solution to be analyzed and said solution of one of NADP or NAD are simultaneously injected into said injection end.

9. The method of claim 1, wherein said concentration of one or more of said $NH_4^+$, NADH and NADPH is determined physically.

10. The method of claim 1, further comprising the step of subjecting a control sample of said L-α-aspartyl-L-phenylalanine methyl ester in aqueous solution consecutively to steps (B)(ia), (B)(ib) and (C), whereby a background value is obtained, and subtracting said background value from said measured value.

11. The method of claim 1, further comprising the step of subjecting a control sample of said L-α-aspartyl-L phenylalanine methyl ester in aqueous solution consecutively to steps (B)(ii) and (C), whereby a background value is obtained, and subtracting said background value from said measured value.

12. A method for the quantitative determination of L-α-aspartyl-L-phenylalanine methyl ester in aqueous solution, comprising:
   (A) enzymatically cleaving said L-α-aspartyl-L-phenylalanine methyl ester into aspartate and phenylalanine methyl ester;
   (B) providing reaction products either
     (ia) by enzymatically cleaving said phenylalanine methyl ester into phenylalanine and methanol and (ib) reacting said phenylalanine with NAD+ in the presence of a phenylalanine dehydrogenase to produce phenylpyruvate, NH$_4$+ and NADH or (ii) by reacting said aspartic acid with NADP+ in the presence of a cell extract which catalyzes the NADP+-dependent conversion of aspartic acid in the presence of NADP+ to produce an aspartic reaction product, NH$_4$+ and NADPH;

and (C) measuring the concentration of at least one of said reaction products to obtain a measured value therefor.

* * * * *